US011214280B2

(12) United States Patent
Myers et al.

(10) Patent No.: US 11,214,280 B2
(45) Date of Patent: Jan. 4, 2022

(54) AUTONOMOUS VEHICLE PROVIDING DRIVER EDUCATION

(71) Applicant: Ford Global Technologies, LLC, Dearborn, MI (US)

(72) Inventors: Scott Vincent Myers, Dearborn, MI (US); Parsa Mahmoudieh, Dearborn, MI (US); Jinesh J. Jain, Dearborn, MI (US); Connie Zeng, Dearborn, MI (US); Maryam Moosaei, Dearborn, MI (US); Mohamed Ahmad, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 198 days.

(21) Appl. No.: 16/479,961

(22) PCT Filed: Jan. 26, 2017

(86) PCT No.: PCT/US2017/015147
§ 371 (c)(1),
(2) Date: Jul. 23, 2019

(87) PCT Pub. No.: WO2018/140022
PCT Pub. Date: Aug. 2, 2018

(65) Prior Publication Data
US 2019/0337532 A1 Nov. 7, 2019

(51) Int. Cl.
*B60W 50/14* (2020.01)
*B60W 30/18* (2012.01)
(Continued)

(52) U.S. Cl.
CPC ............... *B60W 50/14* (2013.01); *A61B 5/18* (2013.01); *A61B 5/6893* (2013.01); *B60W 30/18* (2013.01); *G05D 1/0088* (2013.01); *G09B 19/167* (2013.01); *B60W 2050/146* (2013.01); *B60W 2540/215* (2020.02); *B60W 2540/22* (2013.01);
(Continued)

(58) Field of Classification Search
None
See application file for complete search history.

(56) References Cited

U.S. PATENT DOCUMENTS 9,424,696 B2 * 8/2016 McQuade ................ G07C 9/29
9,665,910 B2 * 5/2017 Chalfant ............... B60W 40/09
(Continued)

*Primary Examiner* — Abdhesh K Jha
(74) *Attorney, Agent, or Firm* — Brandon Hicks; Eversheds Sutherland (US) LLP

(57) ABSTRACT

A method is disclosed for using an autonomous vehicle to teach a student how to drive. The method may include generating, by the autonomous vehicle during a training session, a plan for navigating a section of road. During the training session, the autonomous vehicle may receive control instructions from the student regarding how the student would like to navigate the section of road. If the autonomous vehicle determines that implementing the instructions would be safe and legal, it may implement those instructions. However, if the autonomous vehicle determines that implementing the instructions would not be safe and legal, it may execute the plan. During a training session, an autonomous vehicle may provide on a head-up display to the student certain visual feedback regarding a driving performance of the student.

19 Claims, 4 Drawing Sheets

(51) Int. Cl.
*G05D 1/00* (2006.01)
*A61B 5/18* (2006.01)
*A61B 5/00* (2006.01)
*G09B 19/16* (2006.01)
*G07C 5/02* (2006.01)

(52) U.S. Cl.
CPC ....... *G05D 2201/0213* (2013.01); *G07C 5/02* (2013.01)

(56) References Cited

U.S. PATENT DOCUMENTS

| | | | | |
|---|---|---|---|---|
| 9,783,109 | B2* | 10/2017 | Keaveny | B60Q 9/00 |
| 10,013,893 | B2* | 7/2018 | Harkness | G09B 9/052 |
| 10,077,056 | B1* | 9/2018 | Fields | B60W 50/0098 |
| 10,407,078 | B2* | 9/2019 | Ratnasingam | G05D 1/0011 |
| 10,442,443 | B1* | 10/2019 | Li | B60W 50/10 |
| 10,556,600 | B2* | 2/2020 | James | B60W 40/09 |
| 10,960,859 | B2* | 3/2021 | Takeuchi | G08G 1/166 |
| 2009/0284360 | A1* | 11/2009 | Litkouhi | B62D 15/025 |
| | | | | 340/439 |
| 2012/0224060 | A1* | 9/2012 | Gurevich | B60R 1/00 |
| | | | | 348/148 |
| 2014/0091989 | A1* | 4/2014 | Szczerba | B60R 1/001 |
| | | | | 345/7 |
| 2014/0267263 | A1* | 9/2014 | Beckwith | G06T 15/08 |
| | | | | 345/424 |
| 2014/0267398 | A1* | 9/2014 | Beckwith | G08G 1/166 |
| | | | | 345/633 |
| 2014/0309849 | A1* | 10/2014 | Ricci | G01C 21/26 |
| | | | | 701/33.4 |
| 2015/0241235 | A1* | 8/2015 | Lobato Fregoso | G01C 21/3682 |
| | | | | 701/423 |
| 2015/0262484 | A1* | 9/2015 | Victor | G09B 19/167 |
| | | | | 701/1 |
| 2016/0084661 | A1* | 3/2016 | Gautama | G01C 21/365 |
| | | | | 701/400 |
| 2016/0096531 | A1* | 4/2016 | Hoye | B60W 50/14 |
| | | | | 701/23 |
| 2016/0107597 | A1* | 4/2016 | Won | G08G 1/167 |
| | | | | 340/439 |
| 2017/0370736 | A1* | 12/2017 | Singh | G01C 21/3415 |
| 2018/0017799 | A1* | 1/2018 | Ahmad | H04N 9/3179 |
| 2018/0022385 | A1* | 1/2018 | Fu | B60W 10/20 |
| | | | | 701/41 |
| 2018/0136649 | A1* | 5/2018 | Phillips | G05D 1/0038 |
| 2018/0164108 | A1* | 6/2018 | Rahal-Arabi | G01C 21/3484 |
| 2018/0170377 | A1* | 6/2018 | Tatsukawa | B62D 15/025 |
| 2020/0035124 | A1* | 1/2020 | Li | G09B 19/16 |

* cited by examiner

AUTONOMOUS VEHICLE PROVIDING DRIVER EDUCATION

BACKGROUND

Field of the Invention

This invention relates to vehicular systems and more particularly to systems and methods for providing driver education to a human occupant of an autonomous vehicle.

Background of the Invention

Driver education is a process whereby a human learns how to safely and legally drive a vehicle. In general, a better driver-education process may produce a better driver. Accordingly, what is needed is a system and method for improving driver education.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Figure 1:
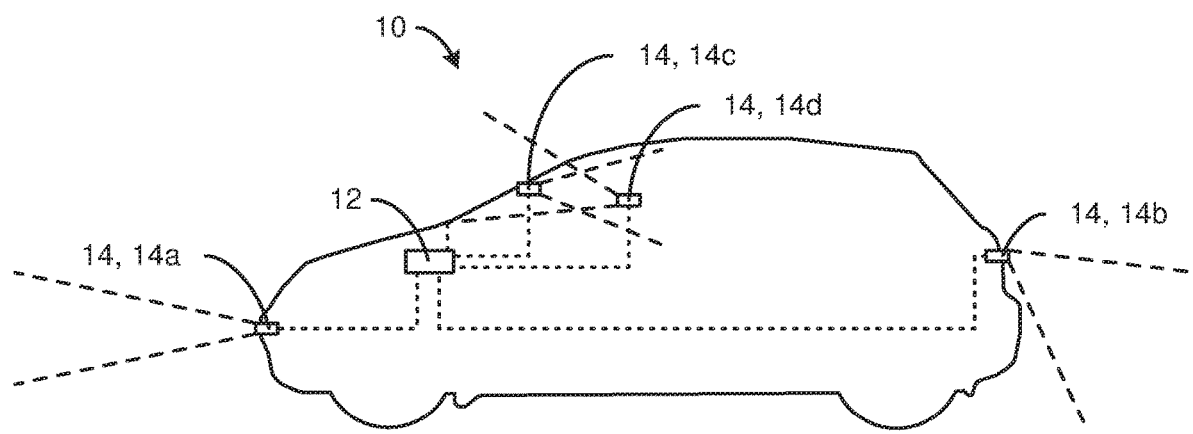
FIG. 1 is a schematic diagram illustrating one embodiment of the technological context within which a system and method for driver education in accordance with the present invention may operate.

Referring to FIG. 1, in selected embodiments, an autonomous vehicle 10 in accordance with the present invention may comprise a computerized system 12 and a plurality of sensors 14. A system 12 may use the outputs of one or more such sensors 14 to determine how best to control various functions or operations of the corresponding autonomous vehicle 10. The sensors 14 included within an autonomous vehicle 10 may take any suitable form. For example, one or more sensors 14 may comprise cameras, lidar devices, radar devices, ultrasonic transducers, accelerometers, gyroscopes, speedometers, thermometers, drive train sensors (e.g., devices for sensing RPM of an engine, wheel slippage, or the like), global positioning system (GPS) devices, or the like, or a combination or sub-combination thereof.

In certain embodiments, a system 12 in accordance with the present invention may control one or more core functions of an autonomous vehicle 10 (i.e., functions that are fundamental to the driving of the autonomous vehicle 10). For example, a system 12 may autonomously control the steering and/or speed of a vehicle 10. Thus, a system 12 may control a collection of components, linkages, actuators, or the like that affect the course taken by the vehicle 10, throttle setting on an engine, braking, or the like or a combination or sub-combination thereof.

Additionally, a system 12 may control one or more peripheral functions of an autonomous vehicle 10 (i.e., functions that are not fundamental to the driving of the autonomous vehicle 10). For example, a system 12 may control the position of one or more seats within a vehicle 10, a climate control system, media settings (e.g., radio stations, television stations, or the like to which a vehicle 10 is tuned), tint of one or more windows, or the like or a combination or sub-combination thereof.

In certain embodiments, one or more sensors 14 in accordance with the present invention may be forward-facing sensors 14a (e.g., cameras, lidar devices, radar devices, ultrasonic transducers, or the like directed to an area ahead of a vehicle 10), rearward-facing sensors 14b (e.g., back-up cameras or lidar devices, radar devices, ultrasonic transducers, or the like directed to an area behind a vehicle 10), side view sensors (e.g., cameras, lidar devices, radar devices, ultrasonic transducers, or the like directed to an area to a side of a vehicle 10), occupant sensors 14c (e.g., cameras directed toward or capturing images of one or more occupants of a vehicle 10), point-of-view sensors 14d (e.g., cameras, lidar devices, radar devices, or the like capturing an occupant's point of view of and/or through a windshield or other window), or the like or a combination or sub-combination thereof.

In selected embodiments, information received, collected, or generated by a system 12 (or portions of a system 12) on-board an autonomous vehicle 10 may be communicated to some hardware located off-board the autonomous vehicle 10. For example, information received, collected, or generated by a system 12 corresponding to an autonomous vehicle 10 may be passed through a communication system to a remote computing device. Accordingly, information received, collected, or generated by a system 12 corresponding to an autonomous vehicle 10 may be accessed by one or more computers off-board the autonomous vehicle 10.

Figure 2:
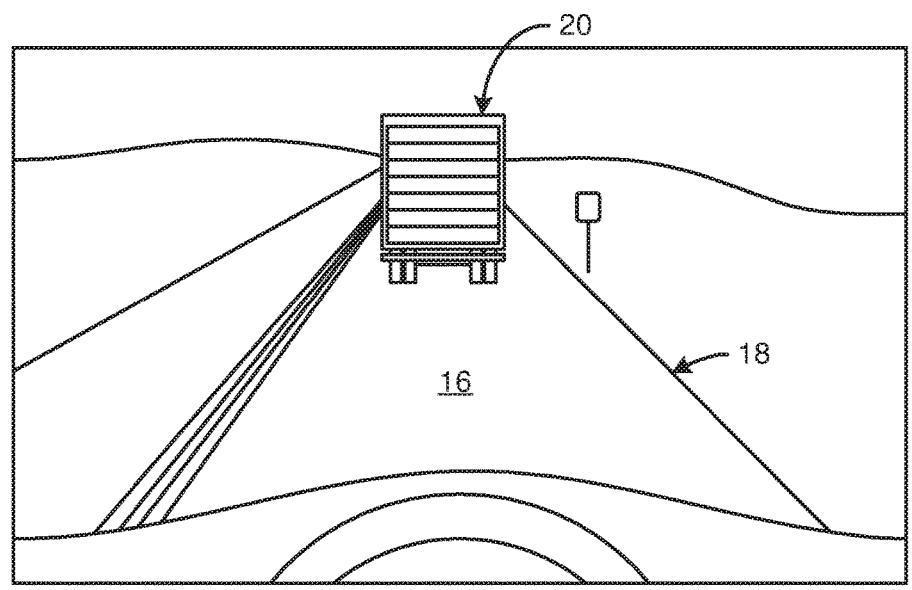
FIG. 2 is a schematic diagram of an exemplary view from the perspective of a student driver through the windshield of an autonomous vehicle in accordance with the present invention.

Referring to FIG. 2, an autonomous vehicle 10 may provide a platform for delivering driver education. Driver education may be a process through which a human student driver is taught how to safely and legally drive a vehicle. To be most effective, driver education may include significant "hands on" training wherein the student driver practices driving the autonomous vehicle 10. During such training, the autonomous vehicle 10 may monitor what is happening in and around the autonomous vehicle 10. Accordingly, should the need arise, the autonomous vehicle 10 may take over control, ignore one or more control inputs or instructions from the student driver, provide audible and/or visual feedback to the student driver, or the like in order to educate the student driver and operate within all applicable safety and legal thresholds.

For example, during a training session, an autonomous vehicle 10 may be traveling within a lane 16 of a roadway 18. The speed and steering of the autonomous vehicle 10 may controlled by the student driver. During such travel, the autonomous vehicle 10 may approach a vehicle 20 that is in the lane 16 ahead of the autonomous vehicle 10. Accordingly, should the student driver approach the vehicle 20 too rapidly, draw too close to the vehicle 20, or the like, the autonomous vehicle 10 may take action.

For example, if there is sufficient time available, the autonomous vehicle 10 may communicate to the student driver the need to slow down, increase the spacing with respect to the other vehicle 20, or the like. If the student responds appropriately, the autonomous vehicle 10 may leave the student driver in control. Conversely, if the student does not respond appropriately or sufficiently, the autonomous vehicle 10 may take further action. This further action may be additional instructions to the student driver to slow down, increase the spacing with respect to the other vehicle 20, or the like.

Should there be insufficient time to communicate a needed change to a student driver or should a student driver fail to respond appropriately after one or more feedback messages are delivered, an autonomous vehicle 10 may take over control of one or more core functions of the autonomous vehicle 10 in order to maintain the autonomous vehicle 10 within applicable safety and legal thresholds. For example, should the student driver approach the vehicle 20 too rapidly, draw too close to the vehicle 20, or the like, the autonomous vehicle 10 may ease off the throttle, apply the brakes, or a combination thereof.

In selected embodiments, when taking action, an autonomous vehicle 10 may only remove control from the student driver in the specific area or areas where change is needed. For example, when speed is the issue, the autonomous vehicle 10 may take over control of the speed of the vehicle 10 and leave steering of the vehicle 10 in the control of the student driver. Conversely, when steering is the issue (e.g., an inappropriate drift within a lane 16), the autonomous vehicle 10 may take over control of the steering of the vehicle 10 and leave the speed of the vehicle 10 in the control of the student driver.

Figure 3:
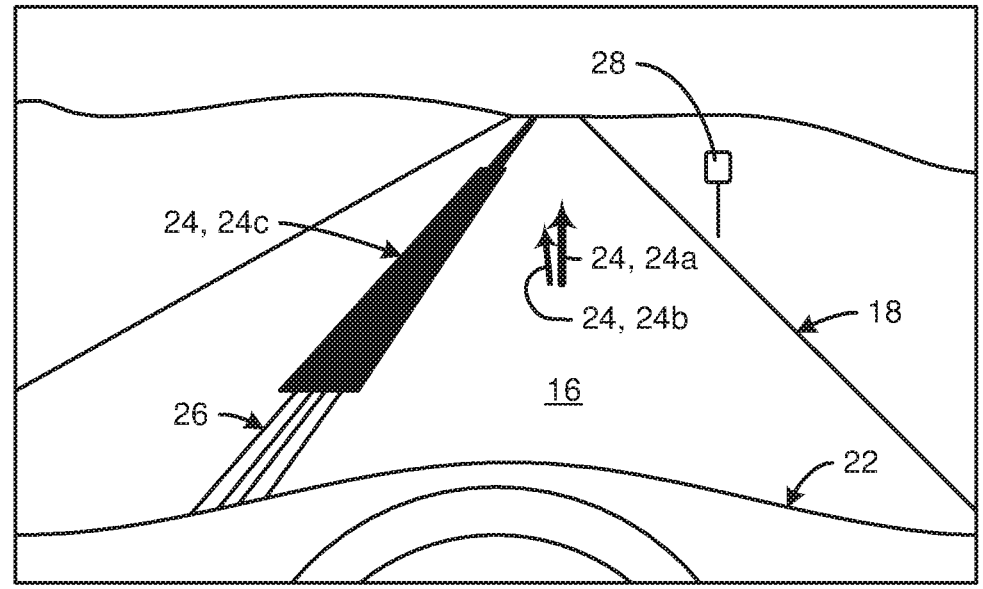
FIG. 3 is a schematic diagram of another exemplary view from the perspective of a student driver through the windshield of an autonomous vehicle, wherein certain feedback is being provided to the student driver via a head-up display in accordance with the present invention.
Figure 4:
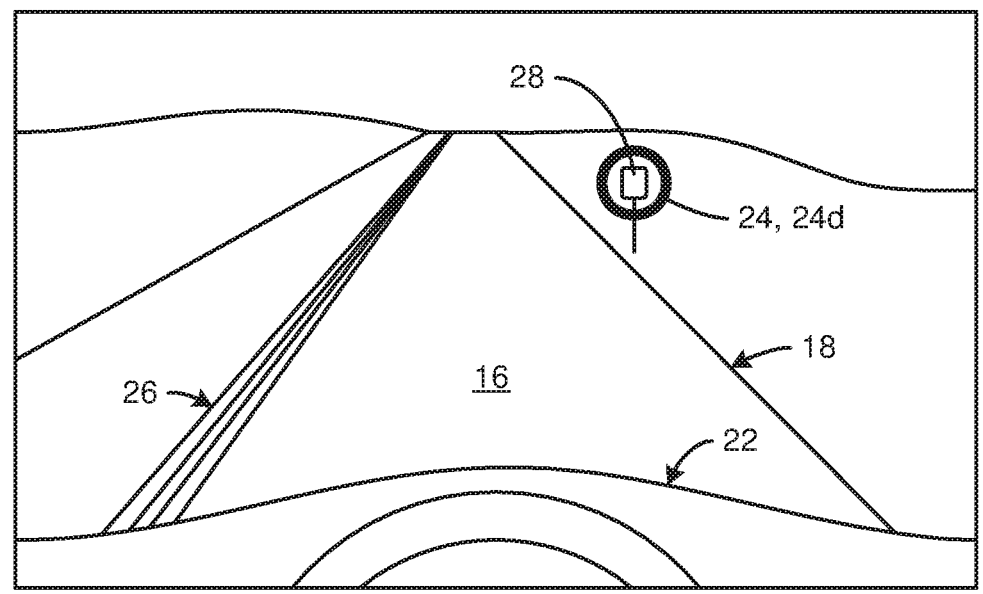
FIG. 4 is a schematic diagram of another exemplary view from the perspective of a student driver through the windshield of an autonomous vehicle, wherein a road sign is being highlighted to the student driver via a head-up display in accordance with the present invention.

Referring to FIGS. 3 and 4, in selected embodiments, an autonomous vehicle 10 may provide feedback to a student driver via one or more channels of communication. For example, feedback may be provided to a student driver visually (e.g., via holographics), audibly (e.g., via computer speech), through other senses of the student driver (e.g., via haptics), or the like or a combination or sub-combination thereof.

In certain embodiments, a student driver may be taught to drive using instructions, feedback, or the like displayed or communicated at least partially via a head-up display. A head-up display may be is a transparent display that presents data to a student driver without requiring the student driver to look away (e.g., toward a dashboard 22 or the instrumentation, displays, or the like thereof) from a driving environment ahead of the autonomous vehicle 10. In selected embodiments, such a transparent display may be independent of a windshield of an autonomous vehicle 10. In other embodiments, a transparent display may be built into or applied onto a windshield of an autonomous vehicle 10.

The data presented on a head-up display may comprise one or more artifacts 24. Artifacts 24 may be numbers, arrows, highlighted regions, or the like that are superimposed, from the perspective of a student driver, over the driving environment the student driver sees through a windshield of an autonomous vehicle 10.

For example, in selected embodiments, a head-up display may train a student driver to stay centered in a lane 16. This may be accomplished by displaying one or more artifacts 24a, 24b. One such artifact 24a (e.g., a center line, center arrow, or the like) may represent or depict an ideal path of the autonomous vehicle 10 in the lane 16. Another artifact 24b may represent or depict an actual path of the autonomous vehicle 10. Accordingly, when a student driver is steering an autonomous vehicle 10 down the ideal path, the two artifacts 24a, 24b may overlap. Conversely, when a student driver is not steering an autonomous vehicle 10 down the ideal path, the artifact 24b corresponding to the actual path may be proportionally spaced from the artifact 24a corresponding to the ideal path.

Alternatively, or in addition thereto, a head-up display may train a student driver to stay centered in a lane 16 by displaying one or more artifacts 24c that highlight one or more lane markings 26. For example, should a student driver drift an autonomous vehicle 10 off of an ideal path and toward or onto a lane making 26, an artifact 24c overlaying (i.e., overlaying from the perspective of the student driver) the lane maker 26 may light up, flash, or the like in order to teach the student driver to respect or be more aware of the lane marking 26.

In selected embodiments, one or more artifacts 24 may highlight or draw attention to one or more road signs 28. For example, should an autonomous vehicle 10 detect an important sign 28 (e.g., a stop sign, speed-limit sign, yield sign, or the like), an artifact 24d overlaying or encircling (i.e., overlaying or encircling from the perspective of the student driver) the sign 28 may light up, flash, or the like in order to teach the student driver to respect or be more aware of the sign 28. In certain embodiments, selected artifacts 24 may be "turned off" or left unused as a student driver advances in his or her learning process.

In selected embodiments, an autonomous vehicle 10 may log driving activity of a student driver as well as ground truth data (e.g., data characterizing how the autonomous vehicle 10 perceived a driving environment, how the autonomous vehicle 10 would have navigated a driving environment, or the like or a combination thereof). This may enable a student driver to compare his or her driving performance with the ground truth and learn where he or she needs to improve.

For example, an autonomous vehicle 10 may leverage certain localization and path-following algorithms in order to log a path taken by the student driver. This log may be used on-board the autonomous vehicle 10 to provide feedback to a student driver. For example, in selected situations wherein the error or difference between the control instructions of a student driver and the ideal path or behavior identified by the autonomous vehicle 10 exceeds a "danger threshold," the autonomous vehicle 10 may take control of the core functions away from the student driver and safely park the autonomous vehicle 10. Then, the log (e.g., video playback) may be used to show the student driver where he or she deviated excessively from the ideal path or behavior.

In selected embodiments, a log collected by an autonomous vehicle 10 may be transferred (e.g., uploaded to a remove server via a telecommunications network) by the autonomous vehicle 10 so that it may be accessed by one or more other computers. Accordingly, when a student driver gets home, he or she may utilize a computerize device in his or her possession to see a graph or other output comparing the path he or she took with the ground truth.

In certain embodiments, a student driver may practice driving at home using a matching gaming system that utilizes a vehicle-based record or playback to continue reducing a delta between the path he or she takes and the ground truth path (e.g., the ideal path) until the delta is smaller than a threshold. In this manner, a student driver may practice everything from staying centered in a lane 16 to applying brake pressure at an appropriate location or time before a stop or turn. Thus, systems and methods in accordance with the present invention may provide, support, or enable additional training without the cost or wear associated with use of the autonomous vehicle 10.

In selected embodiments, special rules and training may be used to assist a handicapped driver with extra training tailored to one or more applicable handicaps. Alternatively, or in addition thereto, at the beginning of a training session a student driver may communication or input information identifying one or more driving activities that are particularly difficult for the student. For example, a student driver may indicate that he or she is having difficulty with parallel parking. Accordingly, during the training session, the autonomous vehicle 10 may tailor the driving experience to include more parallel parking opportunities. In this manner, systems and methods in accordance with the present invention may be tailored to better meet the specific needs of specific student drivers.

In selected embodiments, an autonomous vehicle 10 may be configured to receive and properly respond to speech requests from a student driver. Accordingly, during a training session, a student driver may speak a request to practice a particular skill or set of skills. Alternatively, or in addition thereto, during a training session (e.g., while the autonomous vehicle 10 is safely parked), a student driver may speak a request for help, additional information, one or more visual clues (e.g., one or more artifacts 24), or the like.

In certain embodiments, an autonomous vehicle 10 may monitor stress levels of a student driver. Stress may be detected using heartbeat monitors, deep neural networks analyzing one or more images captured by an interior facing camera, or some other method. Accordingly, data collected by one or more occupant sensors 14c (e.g., one or more cameras directed toward or capturing images of a student driver of the autonomous vehicle 10) may be used to characterize the stress level of a student driver. Depending on the stress level detected, a training session may be aborted or the training session may transition to "easier" (e.g., from the perspective of the particular student driver) training methods or activities until the stress level of the student driver has returned to an acceptable level.

Systems and methods in accordance with the present invention may be utilized world-wide by provisioning (e.g., calibrating) for local traffic rules including, but not limited to, driving from the right side of the vehicle 10 and on the left side of the roadway 18.

Figure 5:
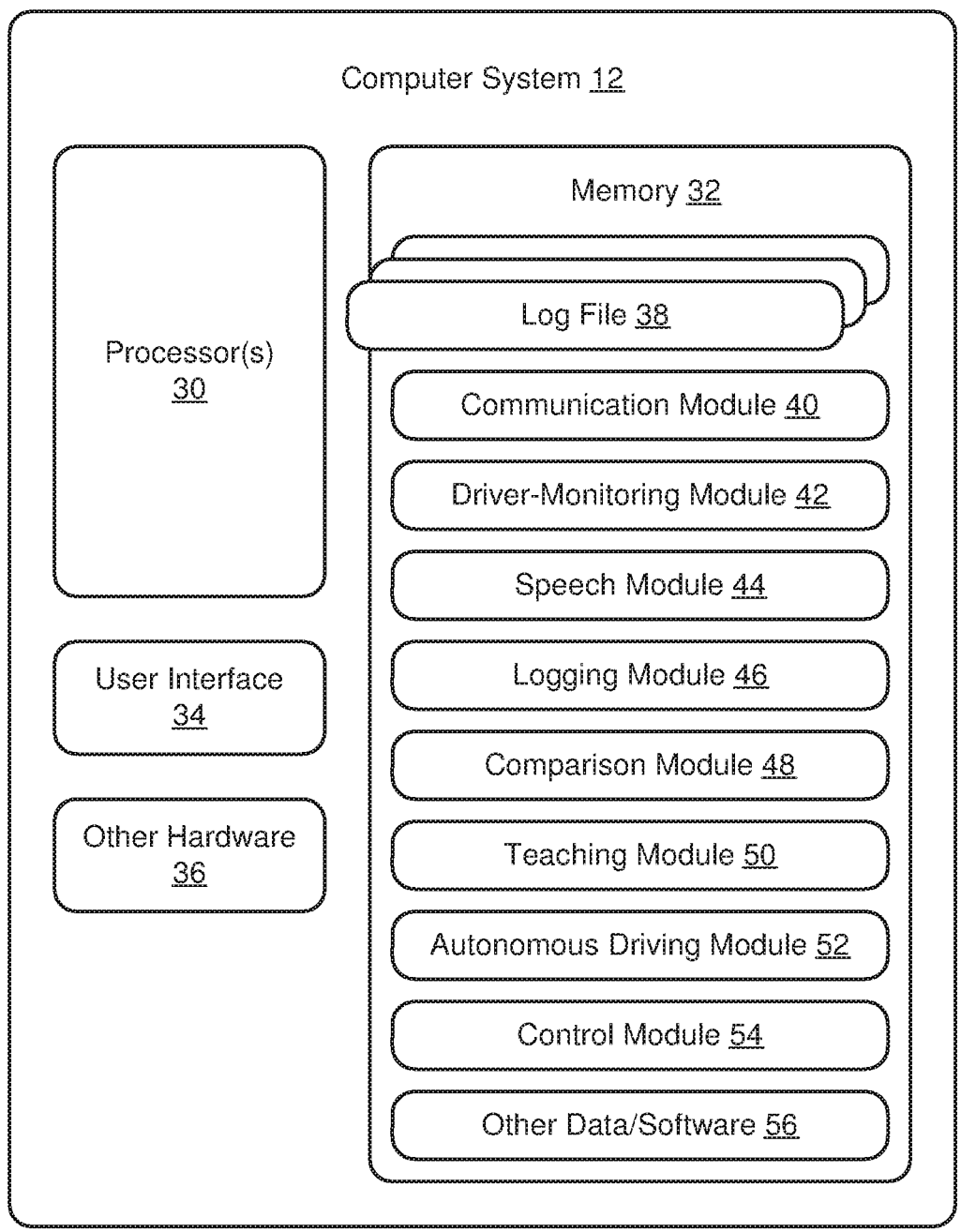
FIG. 5 is a schematic block diagram illustrating one embodiment of a system for providing driver education within an autonomous driving experience in accordance with the present invention.

Referring to FIG. 5, a system 12 in accordance with the present invention may operate in any suitable manner to support customization of an autonomous driving experience. For example, a system 12 may be embodied as hardware, software, or some combination thereof.

In selected embodiments, a system 12 may include computer hardware and computer software. The computer hardware of a system 12 may include one or more processors 30, memory 32, one or more user interfaces 34, other hardware 36, or the like or a combination or sub-combination thereof. In certain embodiments, all or some subset of this computer hardware may be hardware already included as part of an autonomous vehicle 10. That is, all or some portion of the computer hardware may be multipurpose and perform tasks that are already associated with the operation of the autonomous vehicle 10. Alternatively, a system 12 in accordance with the present invention may be dedicated exclusively to enabling, support, and/or providing autonomous driving and selected customization thereof.

The memory 32 of a system 12 in accordance with the present invention may be operably connected to the one or more processors 30 and store the computer software. This may enable the one or more processors 30 to execute the computer software. Thus, a system 12 may augment the functionality or features of an autonomous vehicle 10 by adding and/or modifying software, adding additional hardware to the autonomous vehicle 10, or a combination thereof.

A user interface 34 of a system 12 may enable an engineer, technician, occupant (e.g., student driver), or the like to interact with, run, customize, or control various aspects of a system 12. A user interface 34 may enable a user to manually control (e.g., select, type in, incrementally increase or decrease at the touch of a button or twist of a knob) and/or orally control (e.g., issue one or more commands or requests using his or her voice) one or more settings in order to customize a training session to meet his or her specific needs. In selected embodiments, a user interface 34 of a system 12 may include one or more buttons, switches, knobs, keypads, keyboards, touch screens, pointing devices, microphones, speakers, or video speakers, the like or a combination or sub-combination thereof. Alternatively, or in addition thereto, a user interface 34 may comprise one or more communication ports (e.g., plug in ports, wireless communication ports, etc.) through which one or more external computers or devices may communicate with a system 12 or one or more components thereof.

In selected embodiments, the memory 32 of a system 12 may store (at least temporality) one or more log files 38. A log file 38 may contain information characterizing one or more aspects of a trainings session corresponding to a student driver. For example, a log file 38 may contain data documenting activity of a student driver as well as ground truth data corresponding to that activity. Thus, in certain embodiments, a log file 38 may link the actual path taken by a student driver through a driving environment to an ideal path through that driving environment.

Additionally, the memory 32 may store one or more software modules. For example, the memory 32 may store a communication module 40, driver-monitoring module 42, speech module 44, logging module 46, comparison module 48, teaching module 50, autonomous driving module 52, control module 54, other data or software 56, or the like or a combination or sub-combinations thereof. Alternatively, one or more of the communication module 40, driver-monitoring module 42, speech module 44, logging module 46, comparison module 48, teaching module 50, autonomous driving module 52, and control module 54 may be embodied as hardware or comprise hardware components.

Thus, while FIG. 5 shows the communication module 40, driver-monitoring module 42, speech module 44, logging module 46, comparison module 48, teaching module 50, autonomous driving module 52, and control module 54 as being software-only modules that are stored in memory 34, in actuality, one or more of these modules 40, 42, 44, 46, 48, 50, 52, 54 may comprise hardware, software, or a combination thereof.

A communication module 40 may enable data such as one or more log files 38, software components (e.g., one or more modules 40, 42, 44, 46, 48, 50, 52, 54, or updates thereto), or the like or combinations of sub-combinations thereof to be passed into or out of a system 12 in accordance with the present invention. For example, a communication module 40 forming part of a system 12 carried on-board an autonomous vehicle 10 may enable that system 12 to transfer (e.g., wireless upload) one or more log files 38 generated by the system 12. Alternatively, or in addition thereto, a communication module 40 may enable a system 12 to receive an update to its autonomous driving module 52. Accordingly, improvements developed off-board an autonomous vehicle 10 may be brought on-board as desired or necessary.

A driver-monitoring module 42 may determine a location of the eyes of the student driver with respect to a corresponding autonomous vehicle 10. Knowing the location of the eyes of the student driver with respect to the autonomous vehicle 10 and the location of various features in a driving environment with respect to the autonomous vehicle 10, a system 12 may calculate where to display one or more artifacts 24 in order to interact with (e.g., highlight) those features from the point of view of the student driver. In selected embodiments, a driver-monitoring module 42 may determine a location of the eyes of the student driver with an autonomous vehicle 10 by analyzing one or more images captured by one or more cameras (e.g., occupant sensors 14c in the form of cameras) directed toward the student driver.

In certain embodiments, a driver-monitoring module 42 may use data output by one or more occupant sensors 14c to characterize a stress level of a student driver. This may be done by monitoring one or more biological functions (e.g., facial expressions, eye activity, posture, hand activity, respiration, or the like) of a student driver. For example, in selected embodiments, one or more sensors 14c may collect data on a heart rate of a student driver. Accordingly, by using data output by those sensors 14c, a driver-monitoring module 42 may track a heart rate of the student driver and predict with reasonable precision when the student driver is experiencing significant stress (e.g., stress above a particular threshold).

Alternatively, or in addition thereto, a driver-monitoring module 42 may comprise an artificial neural network (e.g., a deep neural network) trained to detect stress of at least a threshold level in a student driver. The deep learning performed or applied by such an artificial neural network may use one or more algorithms to model high-level abstractions in data corresponding to one or more portions of one or more images collected by the one or more sensors 14c. In selected embodiments, this may be accomplished by using multiple processing layers comprising multiple non-linear transformations.

For example, an artificial neural network may comprise feed-forward computational graphs with input nodes, hidden layers and output nodes. For classifications that involve images, pixel-values of an input image forming part of the classification may be assigned to input nodes, and then be fed through the network, passing a number of non-linear transformations. At the end of the computation, the output node may yield a value that corresponds to the class inferred by the neural network.

In order for an artificial neural network to be able to distinguish between different classes, it needs to be trained based on examples. Accordingly, to create an artificial neural network that is able to classify stress of a student driver, a large collection of example images (e.g., hundreds to thousands of images corresponding to a stress level below a threshold and hundreds to thousands of images corresponding to a stress level above the threshold) having known (e.g., labeled) stress characteristics must be used as training data. Thus, using backpropagation, an artificial neural network may be trained.

A speech module 44 may enable a system 12 to recognize and understand information, commands, requests, or the like provided by a student driver using his or her voice. Accordingly, in selected embodiments, a speech module 44 may provide, enable, or support certain capabilities with respect to automatic speech recognition (ASR) and natural language understanding (NLU). Leveraging such technologies, a speech module 44 may enable one or more speech commands or requests (e.g., words or phrases spoken by a student driver to the autonomous vehicle 10 or one or more systems 12 thereof) to be properly interpreted.

A logging module 46 may be programmed to log driving activity of a student driver as well as ground truth data (e.g., data characterizing how the autonomous vehicle 10 perceived a driving environment, how the autonomous vehicle 10 would have navigated a driving environment, or the like or a combination thereof). In selected embodiments, a logging module 46 may log such information by generating one or more log files 38. Accordingly, a student driver may access one or more log files 38 generated by logging module 46 in order to compare his or her driving performance with the ground truth and learn where he or she needs to improve.

In selected embodiments, one or more log files 38 generated by a logging module 46 may contain one or more video files or be linked to one or more video files captured by one or more sensors 14 (e.g., cameras) of an autonomous vehicle 10. Accordingly, when a student driver accesses one or more log files 38 generated by logging module 46, the student may also be able to access video captured by an autonomous vehicle 10 during a training session. Such video may enable a student driver to more clearly visualize areas where he or she needs to improve.

A comparison module 48 may be programmed to determine whether it would be appropriate (e.g., whether it would be safe and legal) to act on or implement one or more control inputs or instructions received from or corresponding to a student driver. In selected embodiments, this may involve comparing the effects of one or more such control inputs or instructions to one or more rules to determine whether acting on or implementing the one or more control inputs or instructions would violate any of the rules.

If the one or more control inputs or instructions would not violate any rules, then a comparison module 48 may indicate that the one or more control inputs or instructions should be implemented. Conversely, if the one or more control inputs or instructions would violate any rules, then a comparison module 48 may indicate that the one or more control inputs or instructions should not be implemented. For example, the comparison module 48 may indicate that the one or more control inputs or instructions should be ignored and that one or more actions dictated by an autonomous driving module 52 should be implemented.

A teaching module 50 may be programmed to provide feedback to a student driver. In selected embodiments, a teaching module 50 may provide audible and/or visual feedback to the student driver to educate the student driver regarding how to operate within all applicable safety and legal thresholds. For example, if a student driver is approaching another vehicle 20 too rapidly, a teaching module 50 may audibly and/or visually communicate to the student driver the need to slow down, increase the spacing with respect to the other vehicle 20, or the like. In selected embodiments, a teaching module 50 may control a head-up display and the artifacts 24 presented thereon.

An autonomous driving module 52 may be an extensive sub-system programmed to use various informational inputs (e.g., sensor data, images, or the like from one or more sensors 14, GPS data, digital maps, or the like or a combination or sub-combination thereof) to decide how to drive a corresponding autonomous vehicle 10. Accordingly, an autonomous driving module 52 may determine when to speed up, how fast to drive, when to slow down, how hard to brake, when to turn left and how far left, when to turn right and how far right, or the like or any other function or operation for which autonomous control is desired.

An autonomous driving module 52 may have significant latitude in deciding how to navigate the array of options and conditions found in real world driving. Accordingly, when an autonomous driving module 52 decides to navigate a journey, section of road, or the like in a particular manner, that particular manner is usually not the only way the journey, section of road, etc. could have been safely and legally navigated.

For example, an autonomous driving module 52 may decide to take a particular corner at 20 miles per hour. However, given the geometry of the corner and the current road conditions, a speed range for safely and legally taking the corner may be anywhere from about 5 miles per hour to about 25 miles per hour. Thus, the 20 miles per hour decided upon by the autonomous driving module 52 may be one of many acceptable solutions for navigating the corner.

Similarly, an autonomous driving module 52 may decide to take a particular route to a destination. However, given the available roads, multiple routes may enable the autonomous vehicle 10 to reach the destination in a comparable amount of time. Thus, the particular route decided upon by the autonomous driving module 52 may be one of many acceptable routes for reaching the destination.

In selected embodiments, an autonomous driving module 52 may include a plurality of default settings. Default settings may enable an autonomous vehicle 10 to decide how to operate when multiple acceptable options are available. For example, if an algorithm of an autonomous driving module 52 were to consider the geometry of a corner and the current road conditions and determine a maximum safe speed through the corner, a default setting might dictate that an autonomous vehicle 10 navigate the corner at 80% of that maximum speed. Similarly, if a navigation system of an autonomous driving module 52 were to identify multiple possible routes to a destination, a default setting might dictate that an autonomous vehicle 10 take the route requiring the least amount of time.

Accordingly, a student driver may drive an autonomous vehicle 10 differently than an autonomous driving module 52 would and still remain compliant with safety and legal requirements (e.g., remain within certain predetermined physical and legal thresholds). Thus, significant discretion may be granted (e.g., by a comparison module 48) to a student driver so long as no safety or legal requirements are violated.

A control module 54 may be programmed to request, initiate, or implement one or more actions or functions based on one or more determinations made by a comparison module 48, autonomous driving module 52, or a combination thereof. For example, when an autonomous driving module 52 determines that an autonomous vehicle 10 should apply maximum braking, a control module 52 may control one or more actuators to implement that determination.

Figure 6:
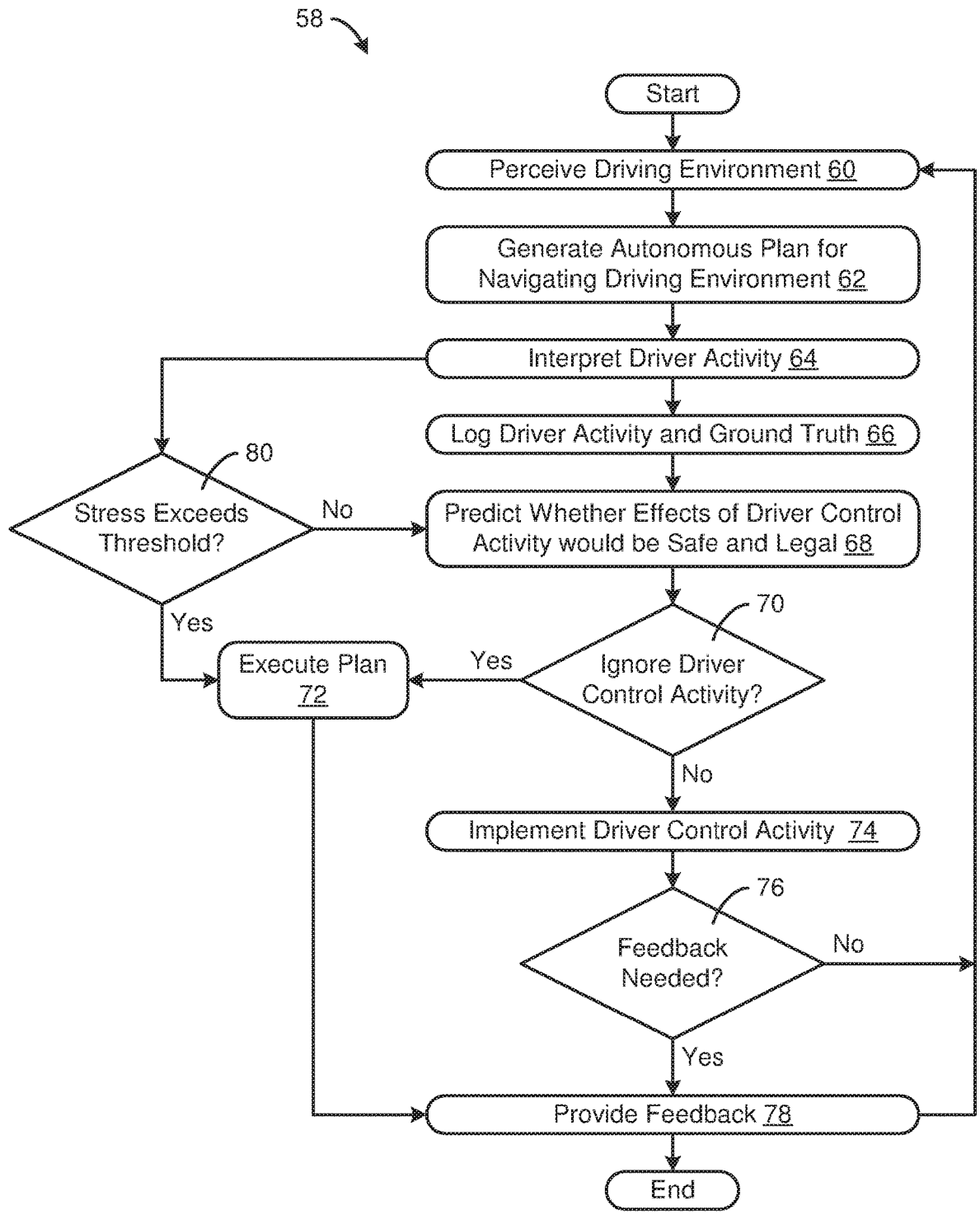
FIG. 6 is a schematic block diagram of one embodiment of a method for providing driver education within an autonomous driving experience in accordance with the present invention.

Referring to FIG. 6, in selected embodiments, a method 58 of conducting driver training with an autonomous vehicle 10 may include perceiving 60 (e.g., via one or more sensors 14) a driving environment surrounding the autonomous vehicle 10. Accordingly, based on its perception of the driving environment, the autonomous vehicle 10 may generate 62 an autonomous plan for navigating the driving environment (e.g., may apply one or more default settings when deciding how to navigate one or more features in a driving environment).

At some point, an autonomous vehicle 10 may interpret 64 driver activity. Such activity may include one or more biological functions such as heart rate or the like. Alternatively, or in addition thereto, such activity may include driver control activity (e.g., one or more control inputs or instructions related to steering, acceleration, braking, or the like) of a student driver. Such control activity and the corresponding ground truth may be logged 66 for future reference.

An autonomous vehicle 10 may predict 68 whether the effects of the driver control activity would be are safe and legal. If an autonomous vehicle 10 predicts 68 that the effects would produce a situation that is unsafe or illegal, the autonomous vehicle 10 may decide 70 to ignore one or more aspects of the driver control activity and execute 72 in their place one or more aspects of the autonomous plan. Conversely, if an autonomous vehicle 10 predicts 68 that the effects would produce a situation that is safe and legal, the autonomous vehicle 10 may decide 70 to implement 74 the driver control activity.

After the driver control activity is implemented 74, a determination may be made 76 as to whether certain feedback should be given to a student driver. If it is decided 76 that feedback is appropriate, the feedback may be provided 78. Such feedback may be positive (e.g., complement the student driver) or negative (e.g., identify an area that needs improvement). After the feedback is provided 78 or if no feedback is to be given, the method 58 may continue and various steps thereof may be repeated. Thus, an autonomous vehicle 10 in accordance with the present invention may be continuously perceiving 60 a driving environment, generating 62 or updating 62 a plan for autonomously navigating the driving environment, and evaluating activity (e.g., control activity) of the student driver.

As some point within a method 58 in accordance with the present invention, a determination may be made 80 as to whether the stress level of a student driver exceeds a stress threshold. For example, in selected embodiments, such a determination may be made 80 in conjunction with (e.g., after) certain driver activity has been interpreted 64. If an autonomous vehicle 10 determines 80 that the stress level of the student driver exceeds a stress threshold, the autonomous vehicle 10 may remove control from the student driver and execute 72 the autonomous plan. This may allow the student driver to relax. Once the student driver is more relaxed, control of the autonomous vehicle 10 may be returned. Conversely, if an autonomous vehicle 10 determines 80 that the stress level of the student driver does not exceed a stress threshold, the autonomous vehicle 10 may leave control of the autonomous vehicle 10 with the student driver.

In general, when an autonomous vehicle 10 removes control from a student driver and executes 72 the autonomous plan (i.e., takes over responsibility for driving the autonomous vehicle 10), there is a need to provide some explanation to the student driver. Accordingly, when an autonomous vehicle 10 removes control from a student driver and executes 72 the autonomous plan, the autonomous vehicle 10 may also provide 78 feedback to the student driver.

The flowchart in FIG. 6 illustrates the architecture, functionality, and operation of possible implementations of systems, methods, and computer-program products according to various embodiments in accordance with the present invention. In this regard, each block in the flowchart may represent a module, segment, or portion of code, which comprises one or more executable instructions for implementing the specified logical function(s). It will also be noted that each block of the flowchart illustration, and combinations of blocks in the flowchart illustration, may be implemented by special purpose hardware-based systems that perform the specified functions or acts, or combinations of special purpose hardware and computer instructions.

It should also be noted that, in some alternative implementations, the functions noted in the blocks may occur out of the order noted in the Figure. In certain embodiments, two blocks shown in succession may, in fact, be executed substantially concurrently, or the blocks may sometimes be executed in the reverse order, depending upon the functionality involved. Alternatively, certain steps or functions may be omitted if not needed.

In the above disclosure, reference has been made to the accompanying drawings, which form a part hereof, and in which is shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," "selected embodiments," "certain embodiments," etc., indicate that the embodiment or embodiments described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors, and may include hardware logic/electrical circuitry controlled by the computer code. These example devices are provided herein purposes of illustration, and are not intended to be limiting. Embodiments of the present disclosure may be implemented in further types of devices, as would be known to persons skilled in the relevant art(s).

At least some embodiments of the disclosure have been directed to computer program products comprising such logic (e.g., in the form of software) stored on any computer useable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

The invention claimed is:

1. A method comprising:
receiving input information from a student driver indicating a first type of driving activity;
generating, by an autonomous vehicle, a plan for performing the first type of driving activity during a first training session;
receiving, by the autonomous vehicle, instructions from the student driver for performing the first type of driving activity during the first training session;
storing, by the autonomous vehicle in memory, a log of a driving performance during the first training session and the plan, the plan including ground truth data relating to how the autonomous vehicle would perform the first type of driving activity;
determining that a difference between the instructions provided by the student driver and a predetermined ideal path or behavior is greater than a threshold amount during a first time period;
switching, based on the determination that the difference is greater than the threshold amount, from a manual driving mode to an autonomous driving mode to autonomously navigate the autonomous vehicle to a parked position; and
presenting, subsequent to autonomously navigating the autonomous vehicle to the parked position, a video playback of a portion of the log associated with the first time period to the student driver.

2. The method of claim 1, further comprising providing visual feedback to the student driver on a head-up display regarding a driving performance of the student driver, wherein the visual feedback corresponds to a deviation of a current location of the autonomous vehicle within a driving lane of an environment from an ideal location of the autonomous vehicle within the driving lane.

3. The method of claim 2, wherein the visual feedback further comprises displaying, by the head-up display from a perspective of the student driver, of a bounded box around a traffic sign within the environment.

4. The method of claim 1, further comprising sending, by the autonomous vehicle, the log to a computing device accessible by the student driver off-board the autonomous vehicle, wherein the log includes video playback of portions of the first training session where the instructions deviated from the plan by a threshold amount.

5. The method of claim 1, further comprising monitoring, by the autonomous vehicle, one or more biological functions of the student driver, and determining, based on the one or more biological functions, a stress level of the student driver.

6. The method of claim 5, further comprising executing, by the autonomous vehicle, the plan when the autonomous vehicle determines that the stress level is above a threshold.

7. A system comprising:
a processor carried on-board an autonomous vehicle; and
memory operably connected to the processor, the memory storing software programmed to:
receive input information from a student driver indicating a first type of driving activity;
generate, during a training session, a plan for navigating a section of road based on the first type of driving activity;
analyze, during the training session, instructions received from the student driver for navigating the section of road based on the first type of driving activity;
store a log of a driving performance during the training session and the plan, the plan including ground truth data relating to how the autonomous vehicle would perform the first type of driving activity;
determine that a difference between the instructions provided by the student driver and a predetermined ideal path or behavior is greater than a threshold amount during a first time period;
switch, based on the determination that the difference is greater than the threshold amount, from a manual driving mode to an autonomous driving mode to autonomously navigate the autonomous vehicle to a parked position; and
present, subsequent to autonomously navigating the autonomous vehicle to the parked position, a video playback of a portion of the log associated with the first time period to the student driver.

8. The system of claim 7, wherein the software is further programmed to monitor one or more biological functions of the student driver and determine a stress level of the student driver based on the one or more biological functions.

9. The system of claim 8, wherein the software is further programmed to execute, by the autonomous vehicle, the plan when the software determines that the stress level is above a threshold.

10. The method of claim 2, wherein the visual feedback includes a first artifact and a second artifact, the first artifact and second artifact being superimposed over a road external to the autonomous vehicle through the head-up display, the first artifact corresponding to an actual path of the autonomous vehicle, and the second artifact corresponding to an ideal path of the autonomous vehicle.

11. The method of claim 1, further comprising:
receiving input information from a student driver indicating a second type of driving activity;
generating, by an autonomous vehicle, a second plan for performing the second type of driving activity during the first training session or a second training session;
receiving, by the autonomous vehicle, instructions from a student driver for performing the second type of driving activity during the first training session or the second training session;
implementing, by the autonomous vehicle, the instructions when the autonomous vehicle determines that doing so would be safe and legal; and
executing, by the autonomous vehicle, the second plan when the autonomous vehicle determines that implementing the instructions would not be safe and legal.

12. The method of claim 2, further comprising:
receiving a request for additional visual feedback from the student driver; and
providing the additional visual feedback to the student driver on the head-up display.

13. The method of claim 1, wherein the plan is calibrated based on a geographic location of the autonomous vehicle.

14. The method of claim 1, wherein executing the plan further comprises initiating autonomous control of only some functions of the autonomous vehicle.

15. A non-transitory computer-readable medium storing computer-executable instructions, that when executed by a processor, cause the processor to perform operations of:
receiving input information from a student driver indicating a first type of driving activity;
generating, by an autonomous vehicle, a plan for performing the first type of driving activity during a first training session;
receiving, by the autonomous vehicle, instructions from the student driver for performing the first type of driving activity during the first training session;
storing, by the autonomous vehicle in memory, a log of a driving performance during the first training session and the plan, the plan including ground truth data relating to how the autonomous vehicle would perform the first type of driving activity;
determining that a difference between the instructions provided by the student driver and a predetermined ideal path or behavior is greater than a threshold amount during a first time period;
switching, based on the determination that the difference is greater than the threshold amount, from a manual driving mode to an autonomous driving mode to autonomously navigate the autonomous vehicle to a parked position; and
presenting, subsequent to autonomously navigating the autonomous vehicle to the parked position, a video playback of a portion of the log associated with the first time period to the student driver.

16. The non-transitory computer-readable medium of claim 15, wherein the computer-executable instructions further cause the processor to perform operations of:
providing visual feedback, wherein the visual feedback includes an artifact displayed on a lane marker of a lane of the autonomous vehicle, wherein the artifact lights-up or flashes based on the autonomous vehicle deviating to within a threshold distance from the lane marker.

17. The non-transitory computer-readable medium of claim 16, wherein the visual feedback further comprises a display, by a head-up display from a perspective of the student driver, of a bounded box around a traffic sign.

18. The non-transitory computer-readable medium of claim 17, further comprising storing, by the autonomous vehicle in memory, a log of the driving performance and the plan, the plan including ground truth data relating to how the autonomous vehicle would perform the first type of driving activity.

19. The non-transitory computer-readable medium of claim 18, further comprising sending, by the autonomous vehicle, the log to a computing device accessible by the student driver off-board the autonomous vehicle, wherein the log includes video playback of portions of the first training session where the instructions deviated from the plan by a threshold amount.

* * * * *